United States Patent [19]

Sarges

[11] Patent Number: 5,011,840
[45] Date of Patent: Apr. 30, 1991

[54] IMIDAZOLIDINEDIONE DERIVATIVES IN DIABETES TREATMENT

[75] Inventor: Reinhard Sarges, Mystic, Conn.

[73] Assignee: Pfizer Inc., New York, N.Y.

[21] Appl. No.: 435,529

[22] PCT Filed: Nov. 24, 1986

[86] PCT No.: PCT/US86/02514
§ 371 Date: May 5, 1989
§ 102(e) Date: May 5, 1989

[51] Int. Cl.$^5$ .................. A61K 31/495; A61K 31/44; C07D 237/30; C07D 471/06

[52] U.S. Cl. .................................... 514/248; 544/237; 546/99; 514/296

[58] Field of Search .................... 544/237; 546/99; 514/296, 248

[56] References Cited

U.S. PATENT DOCUMENTS

| | | | |
|---|---|---|---|
| 3,821,383 | 6/1974 | Sestanj et al. | 514/296 |
| 4,139,532 | 2/1979 | Scheuermann et al. | 514/296 |
| 4,209,527 | 6/1980 | Sarges | 514/296 |
| 4,251,528 | 2/1981 | Brittain et al. | 514/296 |
| 4,782,064 | 11/1988 | Wright, Jr. et al. | 514/296 |

FOREIGN PATENT DOCUMENTS 2064159  7/1971  Fed. Rep. of Germany ...... 514/296

*Primary Examiner*—Mary C. Lee
*Assistant Examiner*—Robert C. Whittenbaugh
*Attorney, Agent, or Firm*—Peter C. Richardson; Paul H. Ginsburg

[57] ABSTRACT

A series of novel 5-substituted imidazolidinedione derivatives and their base salts with pharmacologically acceptable cations are disclosed. These particular compounds are useful in therapy as aldose reductase inhibitors for the control of certain chronic diabetic complications. 5-Naphthalimido-imidazolidine-2,4-dione and 5-[3-(4'-bromo-2'-fluorobenzyl)-3,4-dihydro-4-oxophthalazin-1-yl]-imidazolidine-2,4-dione represent typical and preferred member compounds. Methods for preparing all these compounds from known starting materials are provided.

18 Claims, No Drawings

IMIDAZOLIDINEDIONE DERIVATIVES IN DIABETES TREATMENT

TECHNICAL FIELD

This invention relates to new imidazolidinedione derivatives of interest to those in the field of medicinal chemistry and chemotherapy. More particularly, it is concerned with a novel series of 5-substituted imidazolidinedione compounds for the control of certain chronic complications arising from diabetes mellitus (e.g., diabetic cataracts, retinopathy and neuropathy).

BACKGROUND ART

Past attempts to obtain new and better oral antidiabetic agents have, for the most part, involved an endeavor to synthesize new compounds that lower blood sugar levels. More recently, several studies have been conducted concerning the effect of various organic compounds in preventing or arresting certain chronic complications of diabetes, such as diabetic cataracts, neuropathy and retinopathy, etc. For instance, K. Sestanj et al. in U.S. Pat. No. 3,821,383 discloses that certain aldose reductase inhibitors like 1,3-dioxo-1H-benz[d,e]isoquinoline-2(3H)-acetic acid and some closely-related derivatives thereof are useful for these purposes even though they are not known to be hypoglycemic. These compounds function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of diabetic subjects are prevented or reduced. As a result, these compounds control certain chronic diabetic complications, including those of an ocular nature, since it is already known in the art that the presence of polyols in the lens of the eye leads to cataract formation and concomitant loss of lens clarity.

DISCLOSURE OF THE INVENTION

The present invention relates to novel 5-substituted imidazolidinedione compounds useful as aldose reductase inhibitors for the control of certain chronic complications arising in a diabetic subject. More specifically, the novel compounds of this invention are selected from the group consisting of 5-substituted imidazolidinedione derivatives of the formula:

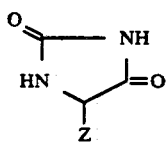

I or a base salt thereof with a pharmacologically acceptable cation, wherein Z is

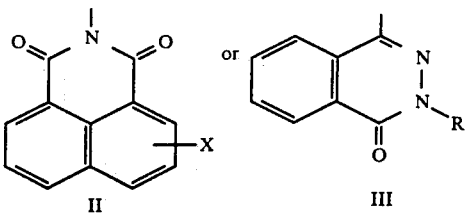

wherein X is hydrogen, fluorine, chlorine, bromine, nitro, trifluoromethyl, $C_1$-$C_4$ alkyl or $C_1$-$C_4$ alkoxy; and R is naphthylmethyl, furfuryl, thenyl or phenylalkyl having from one to three carbon atoms in the alkyl moiety wherein said phenylalkyl is optionally substituted with one or two identical or non-identical substituents on the phenyl ring, said identical substituents being fluorine, chlorine, bromine, trifluoromethyl, $C_1$-$C_4$ alkyl or $C_1$-$C_4$ alkoxy and said non-identical substituents being fluorine, chlorine, bromine, methyl, methoxy or trifluoromethyl. These novel compounds are aldose reductase inhibitors and therefore, possess the ability to reduce or inhibit sorbitol formation in the lens and peripheral nerves of diabetic subjects.

One group of compounds of the present invention of interest is that of the general formula I where Z is of the formula II wherein X is hydrogen, fluorine, chlorine, bromine, nitro, trifluoromethyl, $C_1$-$C_4$ alkyl or $C_1$-$C_4$ alkoxy. Preferred compounds within this group include those where X is hydrogen, chlorine, bromine, nitro, methyl or methoxy.

Another group of compounds of the present invention of interest is that of the general formula I wherein Z is of the formula III wherein R is naphthylmethyl, furfuryl, thenyl, or phenylalkyl having from one to three carbon atoms in the alkyl moiety wherein said phenylalkyl is optionally substituted with one or two identical or non-identical substituents on the phenyl ring, said identical substituents being fluorine, chlorine, bromine, trifluoromethyl, $C_1$-$C_4$ alkyl or $C_1$-$C_4$ alkoxy and said non-identical substituents being fluorine, chlorine, bromine, methyl, methoxy or trifluoromethyl. Preferred compounds within this group include those where R is unsubstituted or ring-substituted phenylalkyl having from one to three carbon atoms in the alkyl moiety and more preferably, R is ring-substituted phenylalkyl having one or two chlorine atoms on the phenyl ring or a bromine atom and a fluorine atom on the phenyl ring (like 2,5-dichlorobenzyl or 4-bromo-2-fluorobenzyl, for example).

Of special interest are such typical and preferred member compounds of the invention as 5-naphthalimido-imidazolidine-2,4-dione and 5-[3-(4'-bromo-2'-fluorobenzyl)-3,4-dihydro-4-oxophthalazin-1-yl]-imidazolidine-2,4-dione, respectively. These two compounds are both potent aldose reductase inhibitors, in addition to being effective in lowering sorbitol levels in the sciatic nerve and lens of diabetic subjects.

DETAILED DESCRIPTION

In accordance with the process employed for preparing the novel compounds of this invention of the general structural formula I wherein Z is of the formula II, an appropriately substituted naphthalic acid anhydride compound of the formula:

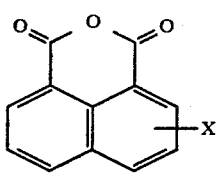

wherein X is as previously defined is condensed with 5-aminohydantoin or a hydrohalide acid addition salt thereof to form the desired 5-substituted hydantoin final product of the structural formula previously indicated. This particular reaction is normally conducted in the presence of an organic base solvent, such as a tertiary amine like pyridine or triethylamine, by heating the two reactants together at a temperature that is in the range of from about 35° C. up to about 120° C. until the condensation is substantially complete, i.e., until no more water of reaction forms and this will usually require a period of at least about one hour. In general, substantially equimolar proportions of reactants are employed, although the ratio can vary anywhere from about 0.5 to about 2.0 mole of 5-aminohydantoin per mole of starting naphthalic acid anhydride compound without causing unwanted side reactions to occur to any significant degree. Upon completion of the reaction, the desired product is then easily isolated from the reaction mixture in a conventional manner, viz., by first concentrating same in vacuo and thereafter triturating the residue with a suitable solvent such as ethanol, followed by further purification via recrystallization from a different solvent such as tetrahydrofuran, for example.

The starting materials required for preparing the novel 5-substituted hydantoin formula I compounds of this invention where Z is of formula II are either known compounds which are readily available commercially, like 1,8-naphthalic acid anhydride, or they are described in the literature like 4-bromo-1,8-naphthalic acid anhydride [H. G. Rule et al., *Journal of the Chemical Society* (London), p. 1764 (1937)] and 3-nitro-1,8-naphthalic acid anhydride [F. Anselm et al. et al., *Chemische Berichte*, Vol. 32, p. 3283 (1899)], or else they can easily be synthesized by those skilled in the art starting from common chemical reagents and using conventional methods of organic synthesis. For instance, 5-aminohydantoin hydrobromide is readily prepared from the known 5-hydroxyhydantoin [J. Abblard et al., *Bulletin de la societe chimique de France*, p. 942 (1971)] via a three-step sequence of reactions that is hereinafter described in detail in the experimental section of the specification (see Preparations A–B).

In accordance with the process employed for preparing the novel compounds of this invention of the general structural formula I wherein Z is of the formula III, an appropriately substituted heteroaromatic aldehyde compound of the formula

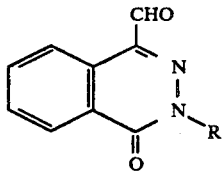

is condensed with an alkali metal cyanide (e.g. sodium cyanide or potassium cyanide) and ammonium carbonate to form the desired 5-substituted imidazolidinedione final product of the structural formula previously indicated. This particular reaction is normally carried out in the presence of an aqueous reaction-inert polar organic solvent medium in which both the reactants and reagents are mutually miscible. Preferred organic solvents for use in this connection include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethyl-formamide, N,N-diethylformamide and N,N-dimethylacetamide, etc. In general, the reaction is conducted at a temperature that is in the range of from about 50° C. up to about 150° C. for a period of about two hours to about four days. Although the amount of reactant and reagents employed in the reaction can vary to some extent, it is preferable to employ at least a slight molar excess of both the alkali metal cyanide and ammonium carbonate reagents with respect to the heteroaromatic aldehyde starting material in order to effect maximum yield. Upon completion of the reaction, the desired product is easily isolated in a conventional manner, e.g., by first diluting the reaction mixture with ice water, followed by acidification to afford the desired 5-substituted imidazolidine compound in the form of a readily-recoverable precipitate. Further purification can then be carried out by such means as silica gel column chromatography and the like, in addition to standard recrystallization procedures.

The aldehyde starting materials (i.e., heteroaromatic aldehyde compounds of structural formula V) are, for the most part, known compounds and can easily be synthesized by those skilled in the art from common organic chemicals by using conventional methods of organic synthesis. For instance, 3-(4'-bromo-2'-fluorobenzyl)-3,4-dihydro-4-oxophthalazine-1-carboxaldehyde is readily prepared from the known 1-methyl-3,4-dihydro-4-oxophthalazine via a four-step sequence of reactions that is hereinafter described in detail in the experimental section of the specification (see Preparations C–F).

The chemical bases which are used as reagents in this invention to prepare the aforementioned pharmaceutically acceptable base salts are those which form non-toxic base salts with the herein described 5-substituted imidazolidinedione compounds such as 5-[3-(4'-bromo-2'-fluorobenzyl)-3,4-dihydro-4-oxophthalazin-1-yl]-imidazolidine-2,4-dione, for example. These particular non-toxic base salts include those derived from such pharmacologically acceptable cations as sodium, potassium, calcium and magnesium, etc. These salts can easily be prepared by simply treating the aforementioned 5-substituted imidazolidinedione compounds with an aqueous solution of the desired pharmacologically acceptable cation, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

As previously indicated, the 5-substituted imidazolidinedione compounds of this inventon are readily adapted to therapeutic use as aldose reductase inhibitors for the control of certain chronic diabetic complications, in view of their ability to reduce lens and peripheral nerve sorbitol levels in diabetic subjects to a statistically significant degree. For instance, 5-[3-(4'-bromo-2'-fluorobenzyl)-3,4-dihydro-7-oxophthalazin-1-yl]-imidazolidine-2,4-dione, a typical and preferred agent of the present invention, has been found to inhibit the formation of sorbitol levels in both the sciatic nerve and lens of diabetic rats to a significantly high degree when given by the oral route of administration at a dose level of 25 mg./kg. Furthermore, the herein described compounds of this invention can be administered by either the oral, topical or parenteral routes of administration. In general, these compounds are ordinarily administered in dosages ranging from about 0.50 mg. to about 50 mg. per kg. of body weight per day, although variations will necessarily occur depending upon the weight and condition of the subject being treated and the particular route of administration chosen.

These compounds may be administered either alone or in combination with pharmaceutically acceptable carriers by the various routes previously indicated, and such administration can be carried out in either single or multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents. In general, the compounds of the invention will be present in such dosage forms at concentration levels ranging from about 0.5% to about 90% by weight of the total composition to provide the desired unit dosage.

For oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various combinations thereof.

For parenteral administration, solutions of these 5-substituted imidazolidinediones in sesame or peanut oil or in aqueous propylene glycol or N,N-dimethylformamide may be employed, as well as sterile aqueous solutions of the corresponding water-soluble, alkali metal or alkaline-earth metal salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection. In this connection, the sterile aqueous media employed are all readily obtainable by standard techniques well-known to those skilled in the art. Additionally, it is also possible to administer the aforesaid 5-substituted imidazolidine compounds topically via an appropriate ophthalmic solution (0.5-2.0%) applied dropwise to the eye.

The activity of the compounds of the present invention, as agents for the control of chronic diabetic complications, is determined by their ability to successfully pass one or more of the following standard biological or pharmacological tests, viz., (1) measuring their ability to inhibit the enzyme activity of isolated aldose reductase; (2) measuring their ability to reduce or inhibit sorbitol accumulation in the sciatic nerve and lens of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

PREPARATION A

A mixture consisting of 2.57 g. (0.022 mole) of 5-hydroxyhydantoin [prepared by reducing parabanic acid (oxalylurea or imidazoletrione) with potassium borohydride according to the method described by J. Abblard et al in *Bulletin de la societe chimique de France,*] p. 942 (1971)] and 30 ml. of thionyl chloride containing three drops of N,N-dimethylformamide was refluxed for a period of approximately 16 hours (overnight). Upon completion of this step, the resulting reaction mixture (which contained 5-chlorohydantoin) was evaporated to dryness under reduced pressure and the residue slurried in 30 ml. of nitromethane, followed by the addition thereto of a solution consisting of 3.3 g. (0.022 mole) of benzyl carbamate dissolved in 50 ml. of nitromethane. After warming the final reaction mixture to 50° C. for a period of three hours, there were obtained, after evaporation and crystallization of the residue from hot water, 1.97 g. (36%) of pure 5-benzyloxycarbonylaminohydantoin, m.p. 178°–180° C. (decomp.); mass spectrum, m/e 249.

Anal. Calcd. for $C_{11}H_{11}N_3O_4$: C, 53.01; H, 4.45; N, 16.86. Found: C, 52.84; H, 4.60; N, 16.89.

PREPARATION B

A mixture consisting of 100 mg. (0.004 mole) of 5-benzyloxycarbonylaminohydantoin (the product of Preparation A) and 1.0 ml. of 30% hydrobromic acid in glacial acetic acid was allowed to stand at room temperature ($\sim 20°$ C.) for a period of 30 minutes. Upon completion of this step., the product was precipitated from the reaction mixture by the addition of diethyl ether and there was obtained 72 mg. (92%) of pure 5-aminohydantoin hydrobromide, m.p. >250° C.; mass spectrum, m/e 115.

Anal. Calcd. for $C_3H_5N_3O_2 \cdot HBr$: C, 18.38; H, 3.08; N, 21.44. Found: C, 18.51; H, 3.04; N, 21.24.

PREPARATION C

In a 250 ml. three-necked, round-bottomed reaction flask equipped with magnetic stirring bar, glass stopper and reflux condenser, there were placed 2.5 g. (0.0156 mole) of 1-methyl-3,4-dihydro-4-oxophthalazine [W. S. Trahanovsky et al., *Journal of Organic Chemistry,* Vol.

31, p. 2033 (1966)] dissolved in 30 ml. of glacial acetic acid, followed by the addition of 34.28 g. (0.0625 mole) of ceric ammonium nitrate dissolved in 120 ml. of glacial acetic acid/water (1:1 by volume). The stirred mixture was then heated in an oil bath at 110° C. for a period of 45 minutes. Upon completion of this step, the reaction mixture was poured into 200 ml. of water containing some ice and thereafter extracted with three-100 ml. portions of ethyl acetate. The combined ethyl acetate extracts were then successively washed with two-50 ml. portions of 2N aqueous sodium hydroxide, two-50 ml. portions of water and one-50 ml. portion of saturated aqueous sodium chloride, followed by drying over anhydrous magnesium sulfate. After removal of the drying agent by means of filtration and the solvent by means of evaporation under reduced pressure, there were obtained 3.76 g. of solid material as the residue. The latter was then dissolved in 100 ml. of hot methanol and chromatographed on a silica gel column, using 20% ethyl acetate/hexane as the eluant. The column had been prepared by first adding three teaspoonfuls of silica gel (70-120 mesh size) to the hot methanolic solution, followed by concentration in vacuo and then drying of the resulting residue under a high vacuum. The dried material was next added to a gravity column (230 mm.×70 mm.) and eluted with the aforesaid eluant, collecting 25 ml. fractions. Fraction Nos. 127-340 were combined and subsequently concentrated in vacuo to yield 436.5 mg. (16%) of 3,4-dihydro-4-oxophthalazine-1-carboxaldehyde; mass spectrum, m/e 174.1 (100%).

Anal. Calcd. for $C_9H_6N_2O_2 \cdot 0.125H_2O$: C, 61.28; H, 3.57; N, 15.88. Found: C, 61.46; H, 3.40; N, 15.85.

PREPARATION D

In a 50 ml. round-bottomed reaction flask equipped with magnetic stirring bar and nitrogen-inlet tube, there were placed 436.5 mg (0.0025 mole) of 3,4-dihydro-4-oxophthalazine-1-carboxaldehyde (the product of Preparation C) and 10 ml. of pure methanol (HPLC grade), followed by the addition of two drops of concentrated sulfuric acid. The resulting mixture was then stirred at room temperature (~20° C.) for a period of four hours. Upon completion of this step, the reaction mixture was filtered to recover the precipitated white solid material, which was thereafter dried in a vacuum to constant weight. In this manner, there was eventually obtained 124.8 mg. (23%) of the dimethyl acetal of 3,4-dihydro-4-oxophthalazine-1-carboxaldehyde; mass spectrum, m/e 221.0, 189.1 (100%).

PREPARATION E

In a dry 50 ml. three-necked, round-bottomed flask reaction flask equipped with magnetic stirring bar, nitrogen-inlet tube, rubber septum and glass stopper, there was placed 40.8 mg. (0.00085 mole) of sodium hydride and 3 ml. of dry tetrahydrofuran, followed by the addition of 124.8 mg. (0.00057 mole) of the dimethyl acetal of 3,4-dihydro-4-oxophthalazine-1-carboxaldehyde (the product of Preparation D) dissolved in 6 ml. of dry tetrahydrofuran. The resulting mixture was then stirred for a period of 30 minutes, followed by the addition of 168.1 mg. (0.00063 mole) of 4-bromo-2-fluorobenzyl bromide in 3 ml. of dry tetrahydrofuran. The final reaction mixture was then stirred at room temperature (~20° C.) for a period of 18 hours prior to the work-up. This was accomplished by first diluting the reaction mixture with 1N hydrochloric acid/water (2 ml./10 ml.) and then extracting the diluted mixture with three-10 ml. portions of ethyl acetate. The organic extracts were then combined and dried over anhydrous sodium sulfate. After removal of the drying agent by means of filtration and the solvent by means of evaporation under reduced pressure, there was obtained, after first drying in vacuo, 240.0 mg. of a yellow solid as the residual material. This material was then chromatographed on a silica gel flash column (20 mm.×175 mm.), using a gradient solvent system beginning with 10% ethyl acetate/hexane (200 ml.), then 20% ethyl acetate/hexane as the eluant and collecting 5 ml. samples. Fraction Nos. 35-50 were combined and subsequently concentrated in vacuo to yield 110.1 mg. (32%) of the dimethyl acetal of 3-(4'-bromo-2'-fluorobenzyl)-3,4-dihydro-4-oxophthalazine-1-carboxaldehyde; mass spectrum, m/e 406.1, 408.1 (m+2), 188.9, 175.1, 75.0 (100%).

PREPARATION F

The procedure described in Preparation E is repeated except that 2,5-dichlorobenzyl bromide is the alkylating agent of choice employed in lieu of 4-bromo-2-fluorobenzyl bromide, using the same molar proportions as before. In this particular case, the corresponding final product obtained is the dimethyl acetal of 3-(2',5'-dichlorobenzyl)-3,4-dihydro-4-oxophthalazine-1-carboxaldehyde.

PREPARATION G

In a 25 ml. round-bottomed reaction flask containing a magnetic stirring bar, there were placed 110.1 mg (0.00027 mole) of the dimethyl acetal of 3-(4'-bromo-2'-fluorobenzyl)-3,4-dihydro-4-oxophthalazine-1-carboxaldehyde (the product of Preparation E) and 5 ml. of trifluoroacetic acid, and the resulting solution was stirred at room temperature (~20° C.) for a period of 15 minutes. Upon completion of this step, the resulting reaction mixture was concentrated in vacuo and the brown solid material so obtained was subjected to silica gel column chromatography. This was accomplished by passing the material through a short silica gel gravity column (130 mm.×12 mm.), using 20% ethyl acetate/hexane as the solvent for the column and as the eluant for same. In this manner, there was obtained, after combining the desired fractions, concentrating in vacuo and drying under a high vacuum, 92.7 mg. (95%) of pure 3-(4'-bromo-2'-fluorobenzyl)-3,4-dihydro-4-oxophthalazine-1-carboxaldehyde; mass spectrum, m/e 360.1, 362.1 (m+2), 103.1 (100%).

PREPARATION H

The procedure described in Preparation G is repeated except that 3-(2',5'-dichlorobenzyl)-3,4-dihydro-4-oxophthalazine-1-carboxaldehyde (the product of Preparation F) is the starting material employed in place of 3-(4'-bromo-2'-fluorobenzyl)-3,4-dihydro-4-oxophthalazine-1-carboxaldehyde, using the same molar proportions as before. In this particular case, the corresponding final product obtained is 3-(2',5'-dichlorobenzyl)-3,4, -dihydro-4-oxophthalazine-1carboxaldehyde.

EXAMPLE 1

A mixture consisting of 250 mg. (0.0013 mole) of 5-aminohydantoin hydrobromide (the product of Preparation B) and 200 mg. (0.001) mole of 1,8-naphthalic acid anhydride in 12.5 ml. of pyridine was heated at 40° C. for a period of eight hours and then at 120° C. for a period of one hour. Upon completion of this step, the resulting reaction mixture was evaporated to dryness under reduced pressure and the residue triturated with ethanol, followed by recrystallization from tetrahydrofuran to ultimately give 160 mg. (54%) of pure 5-naphthalimido-imidazolidine-2,4-dione as the hemihydrate, m.p. 290°–292° C.; mass spectrum, m/e 295.

Anal. Calcd. for $C_{15}H_9N_3.0.5H_2O$: C, 59.21; H, 3.31; N, 13.81. Found: C, 59.44; H, 3.69; N, 13.66.

EXAMPLE 2

The procedure described in Example 1 is repeated except that 4-bromo-1,8-naphthalic acid anhydride [H. G. Rule et al., *Journal of the Chemical Society* (London), p. 1764 (1937)] is the starting material employed in place of 1,8-naphthalic acid anhydride, using the same molar proportions as before. In this particular case, the corresponding final product obtained is 5-(6'-bromonaphthalimido)-imidazolidine-2,4-dione.

EXAMPLE 3

The procedure described in Example 1 is repeated except that 3-nitro-1,8-naphthalic acid anhydride [F. Anselm et al., *Chemische Berichte*, Vol. 32, p. 3283 (1899)] is the starting material employed in place of 1,8-naphthalic acid anhydride, using the same molar proportions as before. In this particular case, the corresponding final product obtained is 5-(5'-nitronaphthalimido)-imidazolidine-2,4-dione.

EXAMPLE 4

In a 50 ml. round-bottomed reaction flask containing a magnetic stirring bar, there were placed 288.3 mg. (0.00079 mole) of 3-(4'-bromo-2'-fluorobenzyl)-3,4-dihydro-4-oxophthalazine-1-carboxaldehyde (the product of Preparation G) and 5 ml. of absolute ethanol, followed by the addition of 104.2 mg (0.0016 mole) of potassium cyanide and 374.6 mg (0.0039 mole) of powdered ammonium carbonate and 5 ml. of water to the stirred suspension. A reflux condenser with a nitrogen-inlet tube was then attached, and the reaction flask and contents were next placed in an oil bath that had been preheated to 70° C. The reaction mixture was then allowed to stir at 70° C. for a period of approximately 16 hours (i.e., overnight), while under a nitrogen atmosphere. Upon completion of this step, the resulting mixture was poured into 30 ml. of ice and water to form a milky yellow suspension having a pH value of pH 11.0. The pH was then carefully re-adjusted to pH 2.0 by the slow addition of 6N hydrochloric acid causing a crystalline precipitate to form. The latter material was subsequently recovered by means of suction filtration and air dried to constant weight, followed by drying under a high vacuum to give 284.8 mg. of a yellow solid. The latter material was then chromatographed on a short silica gel gravity column (130×20 mm.), using 20% ethyl acetate/hexane as the solvent for the column and as the eluant for same, and collecting 5 ml. samples. Fraction Nos. 8–17 were combined and subsequently concentrated in vacuo to yield 101.6 mg. of a crystalline yellow solid. Recrystallization of the latter material from ethyl acetate/petroleum ether then gave 47.6 mg. (14%) of pure 5-[3-(4'-bromo-2'-fluorobenzyl)-3,4-dihydro-4-oxophthalazin-1-yl]-imidazolidine-2,4-dione as a quarter hydrate in the form of a pale yellow solid melting at 184°–186° C. The pure product was further characterized by means of mass spectroscopy and nuclear magnetic resonance data, in addition to elemental analysis.

Anal. Calcd. for $C_{18}H_{12}N_4O_3BrF.0.25H_2O$: C, 49.61, H, 2.89; N, 12.85. Found: C, 49.40; H, 2.93, N, 12.53.

EXAMPLE 5

The procedure described in Example 4 is repeated except that 3-(2',5'-dichlorobenzyl)-3,4-dihydro-4-oxophthalazine-1-carboxaldehyde (the product of Preparation H) is the starting material employed in place of 3-(4'-bromo-2'-fluorobenzyl)-3,4-dihydro-4-oxophthalazine-1-carboxaldehyde, using the same molar proportions as before. In this particular case, the corresponding final product obtained is 5-[3-(2',5'-dichlorobenzyl)-3,4-dihydro-4-oxophthalazin-1-yl]imidazolidine-2,4-dione.

EXAMPLE 6

The following 5-substituted imidzolidinedione derivatives of Examples 1 and 4, respectively, were tested for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In each case, the substrate employed was partially purified aldose reductase enzyme obtained from human placenta. The results obtained with each compound are expressed below in terms of the percent inhibition of enzyme activity with respect to the various concentration levels tested:

| Compound | Percent Inhibition (%) | | | | |
|---|---|---|---|---|---|
| | $10^{-4}M$ | $10^{-5}M$ | $10^{-6}M$ | $10^{-7}M$ | $10^{-8}M$ |
| Product of Ex. 1 | 100 | 59 | 17 | 6 | — |
| Product of Ex. 4 | — | 91 | 86 | 72 | 20 |

EXAMPLE 7

5-[3-(4'-Bromo-2'-fluorobenzyl)-3,4-dihydro-4-oxophthalazin-1-yl]-imidazolidine-2,4-dione, the product of Example 4, was tested for its ability to reduce or inhibit sorbitol accumulation in the sciatic nerve and lens of streptozotocinized (i.e., diabetic rats) by the procedure essentially described in U.S. Pat. No. 3,821,383. In the present study, the amount of sorbitol accumulation in the sciatic nerve and lens of each test animal was measured 27 hours after the induction of diabetes. The compound was then administered orally at 25 mg./kg. at intervals of 4, 8 and 24 hours after the administration of streptozotocin. The results obtained in this manner are presented in terms of the percent inhibition (%) afforded by the test compound as compared to the case where no compound was administered (i.e., the control or untreated animal where sorbitol levels normally rise from approximately 50–100 mM/g. tissue to as high as 400 mM/g. tissue in the 27-hour test period). In this manner, it was found that 5-[3-(4'-bromo-2'-fluorobenzyl)-3,4-dihydro-4-oxophthalazin-1-yl]-imidazolidine-2,4-dione afforded a 61% reduction in the accumulated sorbitol levels in the sciatic nerve of diabetic rats and a 36% reduction in the lens.

What is claimed is:

1. A 5-substituted imidazolidinedione compound of the formula:

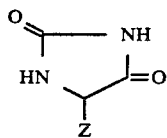

or a base salt thereof with a pharmacologically acceptable cation, wherein Z is

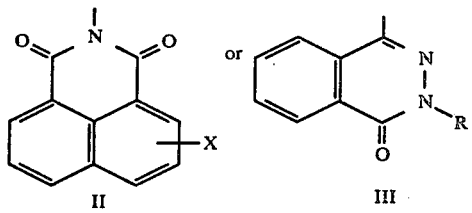

wherein

X is hydrogen, fluorine, chlorine, bromine, nitro, trifluoromethyl, $C_1$-$C_4$ alkyl or $C_1$-$C_4$ alkoxy; and R is naphthylmethyl, furfuryl, thenyl or phenylalkyl having from one to three carbon atoms in the alkyl moiety wherein said phenylalkyl is optionally substituted with one or two identical or non-identical substituents on the phenyl ring, said identical substituents being fluorine, chlorine, bromine, trifluoromethyl, $C_1$-$C_4$ alkyl or $C_1$-$C_4$ alkoxy and said non-identical substituents being fluorine, chlorine, bromine, methyl, methoxy or trifluoromethyl.

2. A compound as claimed in claim 1 wherein Z is of the formula II.

3. A compound as claimed in claim 1 wherein Z is of the formula III.

4. A compound as claimed in claim 2 wherein X is hydrogen.

5. A compound as claimed in claim 2 wherein X is chlorine.

6. A compound as claimed in claim 2 wherein X is bromine.

7. A compound as claimed in claim 2 wherein X is nitro.

8. A compound as claimed in claim 2 wherein X is $C_1$-$C_4$ alkyl.

9. A compound as claimed in claim 2 wherein X is $C_1$-$C_4$ alkoxy.

10. A compound as claimed in claim 3 wherein R is unsubstituted phenylalkyl having from one to three carbon atoms in the alkyl moiety.

11. A compound as claimed in claim 3 wherein R is ring-substituted phenylalkyl having from one to three carbon atoms in the alkyl moiety.

12. A compound as claimed in claim 11 wherein R is ring-substituted phenylalkyl having one or two chlorine atoms on the phenyl ring.

13. A compound as claimed in claim 11 wherein R is ring-substituted phenylalkyl having a bromine atom and a fluorine atom on the phenyl ring.

14. A compound as claimed in claim 13 wherein R is 4-bromo-2-fluorobenzyl.

15. 5-Naphthalimido-imidazolidine-2,4-dione.

16. 5-[3-(4'-Bromo-2'-fluorobenzyl)-3,4-dihydro-4-oxophthalazin-1-yl]-imidazolidine-2,4-dione.

17. A pharmaceutical composition suitable for oral, topical or parenteral administration comprising a pharmaceutically acceptable carrier and a compound as claimed in claim 1 in an amount effective for the treatment of diabetes-associated chronic complications.

18. A method for treating a diabetic subject to prevent or alleviate chronic complications arising in said subject, which comprises administering to said diabetic subject an effective amount of a compound as claimed in claim 1.

* * * * *